(12) United States Patent
Gaytan

(10) Patent No.: US 7,407,927 B2
(45) Date of Patent: Aug. 5, 2008

(54) MASKING AGENT FOR AGRICHEMICALS

(75) Inventor: Jesse Gaytan, Valdosta, GA (US)

(73) Assignee: Arysta LifeScience North America, LLC, Cary, NC (US)

( * ) Notice: Subject to any disclaimer, the term of this patent is extended or adjusted under 35 U.S.C. 154(b) by 642 days.

(21) Appl. No.: 10/067,987

(22) Filed: Feb. 8, 2002

(65) Prior Publication Data

US 2003/0153484 A1    Aug. 14, 2003

(51) Int. Cl.
    *A61K 8/00*     (2006.01)
    *A61K 31/66*     (2006.01)
    *A61L 9/04*     (2006.01)
    *C11D 3/50*     (2006.01)
    *A01N 25/00*     (2006.01)
    *A01N 57/00*     (2006.01)

(52) U.S. Cl. ............... 512/1; 512/4; 514/120; 424/405

(58) Field of Classification Search ............ 512/1, 512/4; 424/76.8, 405, 408; 106/15.05; 514/120
See application file for complete search history.

(56) References Cited

U.S. PATENT DOCUMENTS

| | | | |
|---|---|---|---|
| 3,716,600 A | | 2/1973 | Magee |
| 3,845,172 A | | 10/1974 | Magee |
| 3,914,417 A | | 10/1975 | Magee |
| 4,218,444 A | * | 8/1980 | Koundakjian ............... 514/120 |
| 5,118,506 A | * | 6/1992 | Eichoefer ................... 424/770 |
| 5,298,501 A | * | 3/1994 | Cummings .................. 514/120 |
| 5,369,100 A | * | 11/1994 | Cummings .................. 514/120 |
| 5,645,845 A | * | 7/1997 | Neumann et al. ........... 424/405 |
| 6,207,705 B1 | | 3/2001 | Coats et al. |
| 6,231,865 B1 | | 5/2001 | Hsu et al. |
| 6,337,323 B2 | * | 1/2002 | Cummings et al. ......... 514/120 |
| 2005/0163814 A1 | * | 7/2005 | Gaytan ....................... 424/405 |

FOREIGN PATENT DOCUMENTS

EP               755626 A1 * 1/1997

OTHER PUBLICATIONS

Roger Grant and Claire Grant, *Grant & Hackh's Chemical Dictionary*, 5th ed., McGraw-Hill Book Company, USA, 1987, p. 219.
N. Irving Sax and Richard J. Lewis, Sr., *Hawley's Condensed Chemical Dictionary*, 11th ed., Van Nostrand Reinhold Company, New York, 1987, pp. 471-472.

* cited by examiner

*Primary Examiner*—Jill Warden
*Assistant Examiner*—Keri A Moss
(74) *Attorney, Agent, or Firm*—Pillsbury Winthrop Shaw Pittman LLP

(57) ABSTRACT

Objectionable odors from agrichemicals can be masked by adding one or more terpene or their oxygenated derivatives to the formulation before, during, or after application. A particularly preferred formulation is a granulated insecticide that includes an insecticidal amount of a phosphoroamido(di)thioate in solid form, a polymeric binder, a small amount of an anticking aid, and a masking agent containing an essential oil that is either mixed throughout the granule or sprayed onto its surface. The essential oil masks objectionable odors from the active ingredient without adversely affecting the storage stability or efficacy of the active ingredient.

28 Claims, No Drawings

MASKING AGENT FOR AGRICHEMICALS

FIELD OF THE INVENTION

The present invention relates to a composition and its use as an agriculturally effective active ingredient that exhibits a significant reduction or elimination of unpleasant volatile odors from a field or plot treated therewith.

BACKGROUND TECHNOLOGY

N-hydrocarboyl phosphoroamidothioates and phosphoroamidodithioates (referred to herein as "phosphoroamido(di)thioates") are classes of systemic insecticides that are used in a variety of environments. One of the most commercially important compounds within this class is acephate. Acephate and related compounds are described in U.S. Pat. Nos. 3,716,600, 3,845,172 and 3,914,417. Orthene® is a commercial form of acephate that is produced as a technical grade chemical of about 97 to 99.5% purity. It is available as a liquid and fine powder.

Golf courses and other grassy public areas use acephate to control insects within the grass. The acephate is often applied as a wettable powder or, more recently, as a granule. It is very effective and economical.

Unfortunately, acephate insecticides like sulfur-bearing solid and aromatic solvent-containing liquid agrichemicals can leave an unpleasant, objectionable odor in the treated area. This odor introduces restrictions on the times when the composition can be applied in areas frequented by members of the public.

In past attempts, those in the art have tried to formulate phosphoroamido(di)thioate and other agrichemical compositions with a wide variety of materials to solve the odor problem. None has been commercially viable. One reason for the lack of success with the phosphoroamido(di)thioates is a notorious instability against hydrolysis from residual moisture in a solid formulation and from exposure to elevated temperatures during manufacture, shipment, or storage. The pH of many perfumes and odor reducing agents may also degrade the active ingredient of a formulation after extended storage or exposure to elevated temperatures.

It would be desirable to have a solid composition containing an agriculturally effective phosphoroamido(di)thioate and an odor masking agent that would reduce perception of an objectionable odor in and around an area treated with the phosphoroamido(di)thioate without adversely affecting the stability of the phosphoroamido(di)thioate molecule or its insecticidal efficacy.

It would also be helpful and commercially advantageous to have an agrichemical formulation for sulfur-bearing solid and liquid agrichemicals that hid or masked objectionable odors from human perception in an area treated with the agrichemical without adversely affecting the efficacy of the agrichemically active ingredient.

SUMMARY OF THE INVENTION

It is an objective of the invention to provide a solid formulation and method of manufacture of an insecticidally active phosphoroamido(di)thioate that has at least a more tolerable odor, if not a pleasant odor, than previous solid phosphoroamido(di)thioate formulations.

It is a further objective of the invention to provide a stable formulation of insecticidally active phosphoroamido(di)thioate that is not phytotoxic and is acceptable for application on and around plants.

An additional objective is to provide masking agents that can be used to mask unpleasant odors from agrichemically active ingredients, particularly those in solid form that contain sulfur compounds or in liquid form that contain aromatic petroleum solvents.

In accordance with these and other objectives of the invention that will become apparent from the description herein, the agrichemical formulations according to the invention comprise (a) an agrichemically effective active ingredient that produces objectionable odors and (b) a masking agent comprising a volatile terpene or an oxygenated derivative thereof in a quantity sufficient to mask said odors from said active ingredient. Preferably, the active ingredient and the masking agent are blended, mixed, or otherwise formed into a homogeneous mixture that is applied in one step from a single tank. It is, however, within the invention to apply the active ingredient and the masking agents from separate reservoirs at the same time or in sequential applications.

The preferred formulations of the invention provide a commercially acceptable, storage stable agrichemicals whose unpleasant odors have been masked from perception by humans. Consequently, there is less objection to the continuation of regular activities in and around an area treated by the formulation.

DETAILED DESCRIPTION

The formulations of the invention contain (a) an agrichemically active ingredient, especially an active ingredient that produces objectionable odors, and (b) a masking agent that contains one or more volatile terpenes and/or the oxygenated derivatives thereof in a quantity sufficient to mask objectionable odors from said active ingredient. Optionally, the formulation can contain an aromatic solvent for the active ingredient. The amount of masking agent can be increased to mask additional objectionable solvent odors.

The invention also relates to a method of masking objectionable odors emanating from liquid or solid agriculturally effective active ingredients by blending the masking agent with the active, simultaneously applying the active ingredient and the masking agent from separate reservoirs, or applying the active ingredient and masking agent in sequential steps (i.e., apply the active ingredient first and the masking agent second, or vice versa).

The Agrichemically Effective Active Ingredient

The invention is well suited for agrichemically active formulations that emit noxious or unpleasant odors after treatment of a designated field or area. Such agrichemically effective active formulations are often characterized by a sulfur-containing active ingredient compound (the active ingredient is the source of the odors) or an active ingredient that requires an aromatic hydrocarbon solvent (the solvent is perceived as an unpleasant smell). The masking agent of the present invention will help to hide such odors from human perception so as to make the treated area smell less unpleasant.

Suitable active ingredient formulations that can be used in the present invention comprise an active ingredient that is effective as a herbicide, plant growth regulator, insecticide, fungicide, or essential plant mineral. Those agriculturally effective active ingredients that are particularly well masked are those that contain volatile sulfur-containing compounds. Exemplary agrichemically effective active ingredients that contain sulfur in the molecule and whose odors can be masked with a formulation according to the invention include mercaptan, sulfur, sulfur dioxide, sulfide salts, disulfide salts, methyl sulfometuron, sulfonylurea, cyanfenphos, oryzalin, demeton (I and II), isomethiozin, cyanthoate, tebupirimphos, tebuthiuron, temephos, terbufos, terbutryn, tetradifon, isobornyl thiocyanoacetate, phosphoroamido(di)thioate, and the like.

Solid phosphoroamido(di)thioate formulations are particularly preferred for use with the present invention and comprises (a) insecticidally effective phosphoroamido(di) thioate solids in an amount sufficient to control a target insect population, and (b) a masking agent comprising an essential oil in an amount sufficient to mask phosphoroamido(di)thioate odor from said solids. Optionally a binder is used in an amount sufficient to form a structurally sound granule of said solids and said masking agent. Preferably, the formulation contains 1 to 99.5 wt % phosphoroamido(di)thioate, 0.01 to 2 wt % masking agent, and 0-50 wt % of a binder. More preferably, the formulation contains 75 to 99 wt % phosphoroamido(di)thioate, 0.05 to 1 wt % masking agent, and 0-10 wt % of a binder. Suitable formulations can take the form of granules, powders, or blends of disparate solids.

N-hydrocarboyl phosphoroamidothioates and phosphoroamidodithioates (referred to herein as "phosphoroamido (di)thioates") are classes of particularly heat sensitive compounds that are used as systemic insecticides in a variety of environments. One of the most commercially important compounds within this class is acephate. Acephate and related compounds are described in U.S. Pat. Nos. 3,716,600, 3,845,172 and 3,914,417. Orthene® is a commercial form of acephate that is produced as a technical grade chemical of about 97 to 99.5% purity. It is available as a liquid and fine powder.

The phosphoroamido(di)thioates that can be used in the invention include insecticidally active compounds having the general formula:

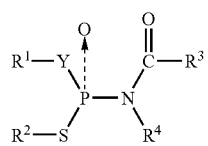

wherein:

$R^1$ and $R^2$ individually are an alkyl, alkenyl or alkynyl group containing up to 6 carbon atoms, $R^3$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^4$ is hydrogen or an alkyl group containing 1 to 6 carbon atoms, and Y is oxygen or sulfur.

Acephate and related compounds are described in U.S. Pat. Nos. 3,716,600, 3,845,172 and 3,914,417. Orthene® is a commercial form of acephate that is produced as a technical grade chemical of about 97 to 99.5% purity. It is available as a liquid and fine powder.

Acephate is a particularly preferred insecticide for use in the present invention. It is commercially available in a technical grade solid of at least 97 wt % purity. The acephate technical is preferably used in as high an amount as possible within a granulated formulation or wettable powder so as to minimize the cost of the product. Preferably, the acephate technical is used in an amount of at least 92 wt %, preferably at least 94 wt %, and most preferably in an amount of at least 95 wt % based on total weight of the dried granule.

Solvent

Solvents are not required for all agrichemically effective active ingredients. Indeed, there is a general desire to avoid petroleum-based and aromatic solvents where possible. The limited solubility of some agrichemicals in alternative solvents and the benefits presented by their use may dictate that such a solvent be used.

There are a wide variety of hydrocarbon solvents available commercially and useful for agrichemicals. Examples of these include aromatics (e.g., AROMATIC 100, AROMATIC 150, or AROMATIC 200 petroleum distillates from Exxonmobil in Houston, Tex.), aliphatics (naphtha or any of the VARSOL products from Exxonmobil), isoparaffins (e.g., any of the ISOPAR products from Exxonmobil) and n-paraffins (e.g., any of the NORPAR products from Exxonmobil). Most are based on petroleum distillates of various boiling points or are mixtures thereof and all produce some amount of objectionable residual odor after application to a designated outdoor area.

In use, an agrichemically effective active ingredient is dissolved in a quantity of the solvent and then diluted, emulsified, or otherwise dispersed in a carrier liquid as a concentrate. This concentrate is packaged and shipped to the point of use. When the product must be applied, the concentrate is added to a mix tank and diluted to the desired concentration of active ingredient for application at a rate within the ranges established by the manufacturer.

The precise amount of the solvent used in the formulation is not generally critical, although one or more active ingredients may have minimum requirements for adequate solubility and the formulation should be sufficiently concentrated (i.e., a maximum solvent concentration) to be economical. In general, the amount of solvent used in a liquid concentrate of an agrichemical active ingredient is within the range from about 0-99 wt % of solvent, preferably 0-95 wt %, and more preferably within the range of 0-80 wt % solvent.

The Masking Agent

The masking agents of the present invention comprise one or more volatile terpene or their oxygenated derivatives that mask at least a substantial portion of the offensive odors from the active ingredient when formulated into a solid granule, mixed into solution, or blended on a solid carrier with a powdered active ingredient, or sprayed onto a co-applied or previously applied active ingredient.

Terpenes are unsaturated hydrocarbons which are based on the isoprene unit of alternating double bonds. Terpenes of preferred use in the invention include citral, camphor, alpha- and beta-pinene, terpineol, limonene, alpha- and beta-terpinene, alpha- and beta-phellandrene, cedrene, geraniol, linalool, neral and abietic acid. Especially preferred terpenes include citral, camphor, alpha- and beta-pinene, terpineol and limonene.

Another source or aromatic terpene are naturally-occurring or synthesized versions of "essential oils". Essential oils are the volatile, aromatic oils obtained by steam or hydro distillation, solvent extraction of botanical sources, pressing of rinds, maceration of flowers and/or leaves in fat and then by solvent extraction of the fat, and enfleurage. Different parts of the plants can be used to obtain essential oils, including the flowers, leaves, seeds, roots, stems, bark, wood, etc. Certain cold-pressed oils, such as the oils from various citrus peels, are also considered to be essential oils. Other aromatic, plant-derived oils are solvent extracted and include Absolutes (hexane followed by ethanol extraction), CO2's (liquid carbon dioxide used as the solvent) and Phytols or Florosols (fluorohydrocarbon solvent). Appropriate definitions are found in Grant & Hackh's *Chemical Dictionary*, 5$^{th}$ ed., p. 219 (1987) and Hawley's *Condensed Chemical Dictionary*, 11$^{th}$ ed. pp. 471-472 (1987) which are incorporated herein by reference to the extent that these definitions are not inconsistent with the disclosure herein.

Essential oils can be synthesized and exist naturally in plants and impart the characteristic odors to flowers, leaves, or woods. They also exist primarily as terpenes (oil of turpentine, juniper, etc) but may be developed from plant constituents by enzyme action or heat. Essential oils are flammable, soluble in alcohol or ether, slightly soluble in water and can contain hydrocarbons, alcohols, phenols, ethers, aldehydes, ketone, and acids. Essential oils are volatile, not greasy, and are unsaponifiable (except for those containing esters). Some essential oils are nearly pure single compounds, e.g., oil of wintergreen (methyl salicylate. Others are mixtures, e.g., turpentine oil (pinene+dipentene) and oil of bitter almond (benzaldehyde+hydrocyanic acid). Those essential oils that contain resin in solution are also called oleoresin or balsams.

Essential oils generally have a boiling point of less than about 150° F. Most essential oils are primarily terpenes and their oxygenated derivatives, e.g., terpene, sesquiterpene, monoterpenol, sesquiterpenol, aldehyde, ketone, ester, etc. While the principle components are mono- to tetra-unsaturated olefin terpenes, essential oils may also contain benzenoid and aliphatic compounds as well including alcohol, ether, carbonyl, etc. functionality. Preferred essential oils can also include such aldehydes as benzaldehyde and cinnamaldehyde. Highly preferred essential oils smell like citrus fruits (orange, lemon, lime, a mixture of lemon and lime, etc.) and pine oil. Specific chemical structure information for the essential oils is available at http://www.essentialoils.org in their chemical reference database, the contents of which is hereby incorporated by reference. A particularly preferred essential oil for use with acephate solids is a lemon fragrance sold by Arrlessence in Atlanta, Ga. USA under the designation "G4136 Lemon Oil" or "AA045486 Lemon". Especially preferred for use are those essential oils that are considered by the USEPA to be "generally regarded as safe" (GRAS).

Essential oils should not be confused with cold-pressed fixed or carrier oils like olive, grapeseed, apricot kernel, etc. Such carrier oils are non-volatile oils composed mainly of fatty acid triglycerides and do not have sufficient volatility or concentration of volatile components to act as an effective masking agent for the phosphoroamido(di)thioate solids according to the present invention.

The masking agent of the present invention may contain water, may be in the form of a soluble salt, dispersible in water, or may be anhydrous depending on the nature of any materials used in additional formulation or forming of the insecticide product.

The masking agent can be combined with the agrichemically active ingredient in virtually any method that allows the masking agent to volatilize with the emission of any noxious odors from the overall formulation. For example, liquid masking agent can be sprayed, poured, or mixed with the agrichemically active solids during the granulation process, dispersed over the active ingredient-containing solids that are distributed at the same time or which were previously distributed or which will be distributed into the treated area, or the masking agent can be mixed with a liquid formulation containing the active ingredient. Conventional equipment can be used: spray nozzles, metering devices, extrusion screws, mixing paddles and the like.

Other Ingredients

A variety of other ingredients can be added to the masked odor formulations of the invention without adversely affecting the perceived odor from a treated area.

As noted above, a binder can be used with solid active ingredients to form a solid granule that can be packaged and used in accordance with conventional granulated forms of the agrichemical active ingredients. Preferably, the binder is soluble in water and/or an organic solvent for dissolution and/or release of the bound components upon exposure to the water or solvent. Even more preferably, the binder is a soluble polymer.

The most preferred water soluble, polymeric binders for use with the present invention are solid at ambient temperatures, inert toward the phosphoroamido(di)thioate active ingredient, and provides lubricity to the extrusion mixture. Suitable polymers include vinylpyrrolidone-vinyl acetate copolymers (such as those sold under the trade name AGRIMER VA-6, available from ISP) and any of the polyalkylene oxides (e.g., polyethylene oxide, polypropylene oxide, and polybutylene oxide) with polyethylene oxide being particularly preferred. Useful amounts of the polymeric lubricant/binder is generally within the range from about 0.1-3 wt % based on total weight of the composition.

An especially preferred binder component for the present invention is polypropylene oxide having an average molecular weight of less than about 50,000. A preferred average molecular weight is within the range from about 15,000 to about 35,000. When used in an amount within the range of 0.2-0.75 wt %, an extrudible mixture is formed that can be readily extruded through a 1-3 mm opening with a temperature rise of no more than a 4° C., and usually less than about 1-2° C.

An anticaking agent can be added, if desired, in an amount sufficient to prevent clumping and caking during the processing and extruding of granules. Generally no more than about 3 wt % is needed. Silica powder in an amount within the range of 0.5-1.25 wt % is particularly useful.

A small amount of water or other solvent is used to dissolve the polymeric binder and provide a lubricious liquid for the active ingredient and any additives used in the formulation. Generally, water or other solvent in an amount of less than 5 wt % based on the total formulation weight is adequate. If added with care and well mixed, water or another solvent can be used in an amount within the range of 0.5-4 wt % and more preferably within the range of 1-3 wt %. Some adjustments up or down may be needed to accommodate ambient humidity within the extrusion facility, i.e., high relative humidity may use added water in the lower ranges (e.g., 0.25-2 wt %) while low relative humidity may find it beneficial to use relatively more added water (e.g., 2-5 wt %) to account for evaporation during manufacture. It is desirable, however, to use as little added water as possible. It is also possible to add a small amount (1-5 wt %) of an alcohol, with or without the formation of an azeotrope, to assist in the dispersion of the essential oil component. It is also possible to add a small quantity of DMSO (dimethylsulfoxide) to provide nonaqueous lubricity for mixing and extrusion.

Preferably, the polymeric binder component is dissolved in the water or other solvent at a concentration within the range of 10-20 wt % polymeric solids and sprayed onto the surface of the agrichemically active solids. Spraying enhances distribution of the polymeric lubricant/binder onto the surface of the solids without incurring the energy costs needed to achieve an equivalent distribution with a mixer blade.

In the preferred manufacturing process, an extrudable mixture of phosphoroamido(di)thioate solids, up to about 3 wt % masking agent, polymeric binder, optional anticaking agent, and a small amount of added water or other solvent for the polymeric binder is passed through an extrusion die having a diameter within the range from about 1-10 mm. The mixture is then extruded into granules at ambient temperatures (e.g., 15° to 22° C.). Importantly, the extrusion is performed in the absence of controlled cooling or heating of the extrusion die and without the introduction of coolant water into the formulation. In the present invention, only so much water or solvent is added as is needed to render the polymeric binder component lubricious and effective as a binder in the final granular product.

The extrudate exiting from the extrusion die can be sliced or cut to length before entering the drier. Suitable driers include convention ovens, fluidized beds, and the like. Use of a fluidized bed operating at a temperature less than the melting point of the technical grade of active ingredient is particularly preferred. Because acephate has a melting point within the range of 63°-67° C., operation of the drier at a temperature of less than 60° C. is useful when granulating acephate.

Extrudates are dried to a moisture content of less than 0.5 wt % and, preferably, to a moisture content of less than 0.3 wt %. Usually, no more than about 10-40 minutes in a fluid bed dryer is required for adequate drying. If not added to the extruder feed, the masking agent can be sprayed onto the dried solids in the form of an anhydrous oil.

The invention claimed is:

1. An agrichemically effective solid formulation in powder or granular form and comprising:
   a. sulfur-containing active ingredient solids in an agrichemically effective amount, wherein said active ingredient solids emit volatile sulfur-based odors that are objectionable to human perception,
   b. 0-90 wt % of an aromatic solvent for said active ingredient, and
   c. about 0.01 to 2 wt % of a masking agent comprising a terpene or oxygenated derivative thereof in an amount sufficient to reduce human perception of objectionable odors from said sulfur-containing active ingredient solids.

2. A formulation according to claim 1 wherein said active ingredient comprises phosphoroamido(di)thioate solids.

3. A formulation according to claim 1 wherein said active ingredient solids comprise acephate and where the masking agent is a lemon essential oil having a lemon fragrance, wherein said essential oil is present in an amount of about 0.05 to 1 wt %.

4. A formulation according to claim 1 wherein said masking agent comprises citral, camphor, alpha-pinene, beta-pinene, terpineol or limonene.

5. A formulation according to claim 1 wherein said masking agent comprises an essential oil.

6. A formulation according to claim 5 wherein said essential oil smells like a citrus fruit.

7. A formulation according to claim 6 wherein said essential oil smells like lemon, lime, or a combination of lemon and lime.

8. A formulation according to claim 5 wherein said essential oil has been synthesized.

9. A formulation according to claim 1 wherein said formulation further comprises a binder.

10. A formulation according to claim 9 wherein said binder is a polymer.

11. A formulation according to claim 10 wherein said binder comprises a polyalkylene oxide.

12. A formulation according to claim 11 wherein said binder comprises a polyethylene oxide.

13. An insecticidally effective formulation in powder or granular form and comprising:
   a. about 1 to 99.5 wt % of phosphoroamido(di)thioate solids in an insecticidally effective amount, wherein said solids emit odors that are objectionable to human perception, and
   b. about 0.01 to 2 wt % of a masking agent comprising a terpene or oxygenated derivative thereof in an amount sufficient to reduce human perception of objectionable odors from said formulation.

14. An insecticidally effective formulation according to claim 13 wherein said masking agent comprises citral, camphor, alpha-pinene, beta-pinene, terpineol or limonene.

15. A formulation according to claim 13 wherein said masking agent comprises lemon essential oil.

16. A formulation according to claim 15 wherein said essential oil smells like citrus fruit.

17. A formulation according to claim 16 wherein said essential oil smells like lemon, lime, or a combination of lemon and lime.

18. A formulation according to claim 15 wherein said essential oil has been synthesized.

19. A formulation according to claim 13 wherein said formulation further comprises a binder.

20. A formulation according to claim 19 wherein said binder is a polymer.

21. A formulation according to claim 20 wherein said binder comprises a polyalkylene oxide.

22. A formulation according to claim 21 wherein said binder comprises a polyethylene oxide.

23. A formulation according to claim 19 wherein said essential oil has been sprayed onto a granule comprising said phosphoroamido(di)thioate solids and said binder.

24. A formulation according to claim 19 wherein said essential oil has been admixed with said phosphoroamido(di)thioate solids and said binder and extruded to form a solid granule.

25. An agrichemically effective formulation comprising:
   a. about 75 to 99 wt % acephate,
   b. a polymeric binder for said active ingredient, wherein said binder comprises a polyalkylene oxide,
   c. 0-90 wt % of an aromatic solvent for said active ingredient,
   d. about 0.05 to 1 wt % of a masking agent comprising a lemon essential oil to reduce human perception of objectionable odors from said acephate.

26. A formulation according to claim 1, wherein said sulfur-containing active ingredient is an extruded solid having less than 5 wt % water, and said masking agent is coated onto said extruded solid.

27. A formulation according to claim 26, wherein said masking agent is sprayed onto said extruded solid and where the masking agent is anhydrous.

28. An agrichemically effective formulation of claim 25, wherein said agrichemically effective ingredient, polymeric binder and aromatic solvent are an extruded solid, and where said masking agent is coated on said extruded solid by spraying.

* * * * *